(12) United States Patent
Claude et al.

(10) Patent No.: US 7,540,859 B2
(45) Date of Patent: Jun. 2, 2009

(54) DIALYSIS VALVE AND METHOD

(75) Inventors: Timothy J. Claude, Coon Rapids, MN (US); Edward A. Barlow, Bloomington, MN (US); David W. Hunter, Minneapolis, MN (US); Michael S. Rosenberg, Eagan, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 804 days.

(21) Appl. No.: 10/497,137

(22) PCT Filed: Apr. 22, 2004

(86) PCT No.: PCT/US2004/012438

§ 371 (c)(1),
(2), (4) Date: Aug. 18, 2004

(87) PCT Pub. No.: WO2004/093937

PCT Pub. Date: Nov. 4, 2004

(65) Prior Publication Data

US 2005/0038396 A1 Feb. 17, 2005

Related U.S. Application Data

(60) Provisional application No. 60/464,778, filed on Apr. 23, 2003.

(51) Int. Cl.
*A61M 5/00* (2006.01)

(52) U.S. Cl. .............................. 604/246; 604/6.1; 251/4

(58) Field of Classification Search ................ 604/4.01, 604/6.01, 6.16, 9, 96.01, 99.02, 100.03, 102.03, 604/103.08, 103.09, 167.01–167.06, 207, 604/246–247, 249–250, 500, 507, 524, 526, 604/527, 890.1, 891.1; 606/158; 251/5, 251/4, 7, 8, 129.06

See application file for complete search history.

(56) References Cited

U.S. PATENT DOCUMENTS

| | | | |
|---|---|---|---|
| 3,685,786 A | 8/1972 | Woodson | 251/4 |
| 4,267,835 A | 5/1981 | Barger et al. | 128/214 E |
| 4,546,499 A | 10/1985 | Possis et al. | 623/1 |
| 4,562,597 A | 1/1986 | Possis et al. | 623/1 |
| 4,601,718 A | 7/1986 | Possis et al. | 623/1 |
| 4,671,320 A * | 6/1987 | Grifols Lucas | 137/556.3 |
| 5,102,389 A | 4/1992 | Hauser | |
| 5,338,313 A | 8/1994 | Mollenauer et al. | 604/249 |
| 5,498,338 A * | 3/1996 | Kruger et al. | 210/641 |
| 5,514,109 A | 5/1996 | Mollenauer et al. | 604/249 |
| 5,556,387 A | 9/1996 | Mollenauer et al. | 604/249 |
| 5,797,879 A | 8/1998 | DeCampli | |
| 6,053,901 A | 4/2000 | Finch, Jr. et al. | |
| 6,302,905 B1 * | 10/2001 | Goldsteen et al. | 623/1.1 |
| 7,025,741 B2 | 4/2006 | Cull | |
| 2001/0021872 A1 | 9/2001 | Bailey et al. | |
| 2003/0014003 A1* | 1/2003 | Gertner | 604/5.01 |
| 2003/0069646 A1 | 4/2003 | Stinson | 623/23.7 |

* cited by examiner

*Primary Examiner*—Kevin C Sirmons
*Assistant Examiner*—Emily Wachtel
(74) *Attorney, Agent, or Firm*—Fish & Richardson P.C.

(57) ABSTRACT

A dialysis valve includes a tube attached between an artery and a vein which, when elongated, simultaneously narrows in diameter at at least one location. The narrowed portion of the tube decreases the volume and velocity between the arterial and venous side of the patient to prevent damage or intimal hyperplasia on the venous side between dialysis treatments. When the valve is opened for dialysis, an unrestricted blood flow exists between the arterial and venous side, permitting a controlled, open blood flow during dialysis.

22 Claims, 7 Drawing Sheets

DIALYSIS VALVE AND METHOD

FIELD OF THE INVENTION

The present invention relates to a valve useful for controlling blood flow in artificial dialysis fistulas or bypass grafts.

BACKGROUND

Dialysis involves connecting patients with insufficient kidney function to a dialysis machine which cleanses the blood of waste products and impurities. Put another way, the dialysis machine performs the same function as a normal, healthy kidney should. In other cases, dialysis is used to remove poisons and drugs from the blood more safely and quickly than the natural kidneys would. To properly connect a patient to a dialysis machine requires accessing, on a continuing basis, a blood vessel, to divert the flow of blood from the patient to the dialysis machine. This is normally accomplished by the implantation into the patient of an artificial fistula or bypass graft, which is usually made of expanded polytetrafluoroethylene (ePTFE). In the case of a graft, the graft is punctured with a needle and blood from patients requiring dialysis is transported to the dialysis machine whereupon the blood is diffused across a semipermeable membrane. Upon completion of this procedure, dialyzed blood is returned to the patient through a second needle in the graft. Dialysis is usually necessary every two to three days, which often results in the lumen of the graft becoming compromised. The more common problem related to dialysis grafts is intimal hyperplasia, which can occur when the higher pressure/volume of the arterial flow crosses the boundary from the relatively non-compliant graft to the more compliant outflow vein at the venous anastomosis. The resultant intimal hyperplasia in the vein adjacent to the anastomosis leads to progressive stenosis and eventually premature clotting and graft occlusion. Repairing a hemodialysis graft occlusion is currently accomplished by one of several techniques: open surgical revision (surgical thrombectomy), thrombolytic drugs (thrombolysis) or mechanical declotting via percutaneous techniques (percutaneous mechanical thrombectomy). Percutaneous mechanical thrombectomy techniques include suction thrombectomy, balloon thrombectomy, clot maceration and mechanical thrombectomy. The goal of each of these therapies is the preservation of vascular access. In almost all cases, any technique which is used to declot the graft will also require angioplasty of the venous anastomotic stenosis in order to reestablish normal flow.

It is known that blood flow in excess of 300 cc per minute can cause intimal hyperplasia in the outflow vein near the anastomosis. The problem arises from the fact that blood flows less than 300 cc per minute have been associated with graft thrombosis. The solution to this dilemma appears to arise from a recognition that blood flows of less than 300 cc per minute are not intrinsically pro-thrombotic, but are a reflection of progressive stenosis that is likely to rapidly reach a level at which thrombosis can occur with any added insult. What would be ideal and what is clearly needed is a method for preventing high flows through the graft while it is not being used and thus reducing or eliminating the stimulus for intimal hyperplasia and yet allowing the high flows through the graft during dialysis that are required for a successful dialysis run.

SUMMARY

In one embodiment the invention comprises a method of controlling blood flow during dialysis. The method involves implanting a tube between a patient's vein and an artery, where the tube is capable of containing fluids and defines a longitudinal dimension, a diameter and an inner surface. The diameter of the tube is narrowed during dialysis at at least one location along the longitudinal dimension to control the volume and velocity of blood flow through the tube during dialysis. In another embodiment, the inner surface of the tube at the narrowed location is in a substantially circular configuration.

In another embodiment the invention comprises a dialysis valve, the valve comprising a tube capable of containing fluids and defining a longitudinal dimension, a diameter and an inner surface. A bellows capable of being held at varying lengths defines an interior chamber wherein the tube is mounted in the chamber so that when the bellows increases in length, the tube simultaneously increases in longitudinal dimension and at least a portion of the tube decreases in diameter. In a further embodiment the tube comprises a braided nitinol structure processed to exhibit superelasticity below normal human body temperature coated with an elastomer allowing the tube to be repeatedly altered in longitudinal dimension and in diameter and still maintain fluid containing capability.

In still another embodiment the invention comprises a dialysis valve, the valve comprising a tube capable of containing fluids and defining a longitudinal dimension, a diameter and an inner surface. A balloon contacts the tube so that when the balloon is inflated at least a portion of the tube decreases in diameter. In a further embodiment, the tube comprises a braided nitinol structure processed to exhibit superelasticity below normal human body temperature coated with an elastomer allowing the tube to be repeatedly altered in longitudinal dimension and in diameter and still maintain fluid containing capability. In yet a further embodiment the balloon surrounds the tube.

In an alternative embodiment the invention comprises a valve, the valve comprising a tube capable of containing fluids and defining a longitudinal dimension, a diameter and an inner surface. A nitinol spring is attached to each end of the tube so that when the spring is actuated the tube decreases in longitudinal dimension and the tube increases in diameter. In a further embodiment the tube comprises a braided nitinol structure processed to exhibit superelasticity below normal human body temperature coated with an elastomer allowing the tube to be repeatedly altered in longitudinal dimension and in diameter and still maintain fluid containing capability.

BRIEF DESCRIPTION OF THE DRAWINGS

FIG. 5 shows a cross section of the coated braid assembly shown in FIGS. 3, 3a, 4, and 4a.

DETAILED DESCRIPTION

Definitions
"Braid Assembly" refers to a tubular structure comprised of overlapping flexible strands.
"ePTFE" refers to Expanded Polytetrafluoroethylene.

Nomenclature
10 Uncoated Braid
11 Strand
12 Diameter
14 Longitudinal Dimension
20 Coated Braid Assembly
22 Diameter
24 Longitudinal Dimension
25 Inner Surface
26 Elastomeric Coating
28 Anti-Thrombogenic Coating
30 Fistula Graft (Arterial Side)
31 Bonding Area
32 Fistula Graft (Venous Side)
41 Aperture
42 Outer Housing
43 Chamber
44 Bellows
45 Inter-Wall Space of Bellows
46 Hydraulic Line
47 Inner Wall of Bellows
48 Port
49 Membrane
50 Dialysis Valve (Hydraulic Bellows Actuated)
51 Outer Wall of Bellows
52 Infusion Needle
53 Nipple
54 Floating Connector
55 Fixed Connector
56 Compressible Section
60 Dialysis Valve (Hydraulic Balloon Actuated)
62 Balloon
64 Hydraulic Line
80 Valve
82 Nitinol Spring
83 O Ring
84 Controller
84a Electrical Wire (Signal)
84b Electrical Wire (Ground)
85 Threaded Connector
86 Outer Housing
100 Arm
110 Artery
120 Vein Construction The valve of the present invention applies the principles of fluid dynamics so that as the lumen of a tube is narrowed, the dynamic pressure and volume of fluids passing through it will decrease. Thus, when the principles of fluid dynamics are applied to blood flow, a controlled narrowing in a synthetic dialysis graft decreases arterial dynamic pressure and decreases blood volume in the coated braid assembly 20 before it can impact the lower pressure venous volume in the receiving vein 120. It has been medically documented that a blood flow rate of below 300 cc per minute will, in most cases, prevent intimal hyperplasia from occurring. An-additional advantage of reducing blood flow rate to below 300 cc per minute is that it further reduces the likelihood of problems with peripheral "stealing" of blood from the extremity (e.g., the hand) during the dialysis procedure.

Figure 1:
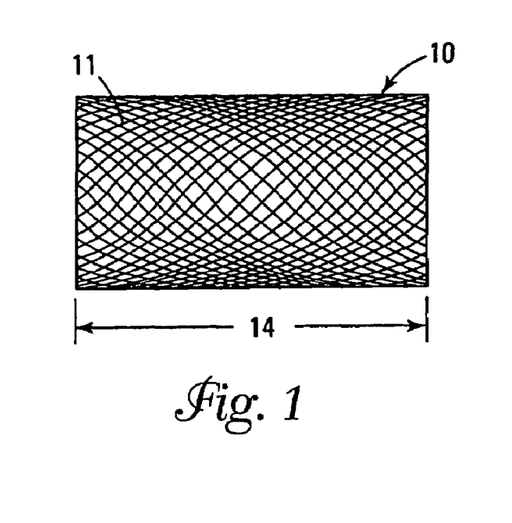
FIG. 1 shows a side view of the uncoated braid in the truncated, open configuration.
Figure 1A:
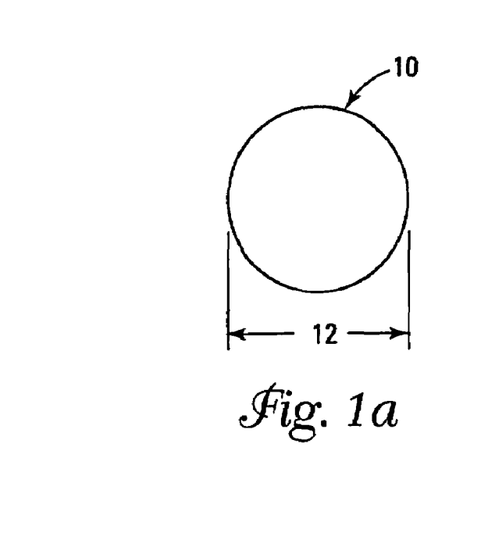
FIG. 1a shows an end view of the uncoated braid shown in FIG. 1.
Figure 2:
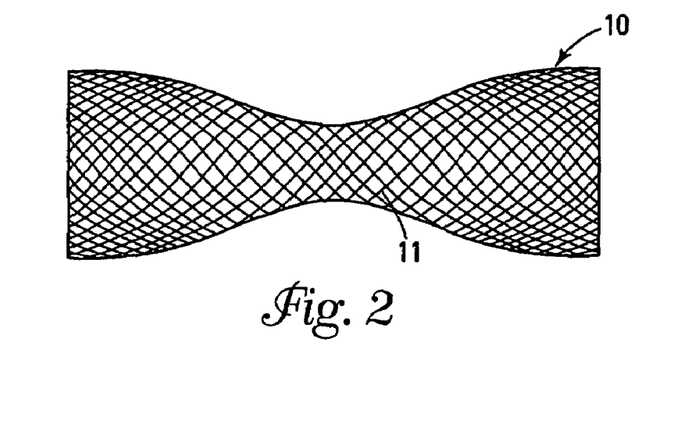
FIG. 2 shows a side view of the uncoated braid in the elongated, decreased diameter configuration.
Figure 2A:
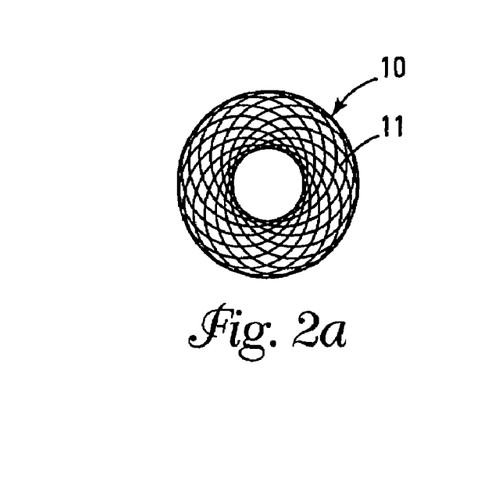
FIG. 2a shows an end view of the uncoated braid shown in FIG. 2.

FIGS. 1, 1a, 2 and 2a show an uncoated tubular braid 10 which defines a diameter 12 and a longitudinal dimension 14. The braid 10 comprises a plurality of individual strands 11 that are crossed over each other to form a cylinder as shown in FIG. 1 when in an unstressed or relaxed state. The diameter 12 and longitudinal dimension 14 of the braid 10 are inversely proportional to each other, wherein as shown in FIG. 2 the braid 10 upon being increased in its longitudinal dimension 14 decreases in at least some portion of its diameter 12. Conversely, as shown in FIG. 1, when the braid 10 is decreased in longitudinal dimension 14 the diameter 12 increases. The braiding pattern as shown in FIGS. 1, 1a, 2 and 2a shows bilateral symmetry wherein a center portion (unnumbered) of the braid 10 decreases in diameter with an increased longitudinal dimension 14. It should be noted, however, that other braiding techniques exist which would cause a different portion (not shown) of the braid 10 to decrease in diameter 12 with an increased longitudinal dimension 14, resulting in a different symmetry. In a preferred embodiment, the braid 10 is made of nitinol strands 11. Nitinol is preferred because of its excellent biocompatibility and more importantly its ability to be repeatedly deformed and reformed without taking a permanent set or kink or breaking due to fatigue resistance. Other materials contemplated by and therefore within the scope of the invention include various grades of stainless steel and composite materials.

Figure 3:
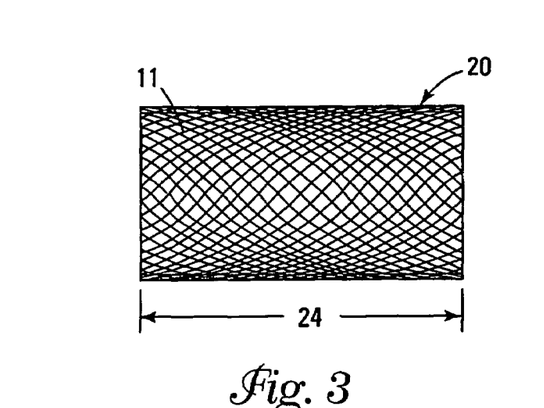
FIG. 3 shows a side view of the coated braid assembly in the shortened, increased diameter configuration.
Figure 3A:
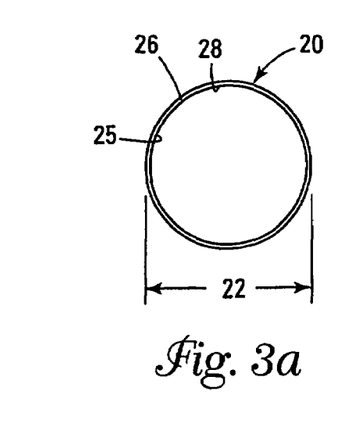
FIG. 3a shows an end view of the coated braid assembly shown in FIG. 3.
Figure 4:
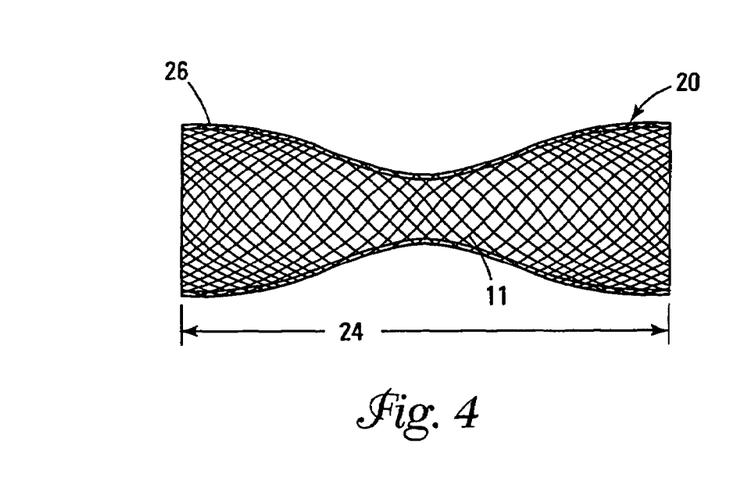
FIG. 4 shows a side view of the coated braid assembly in the elongated, decreased diameter configuration.
Figure 4A:
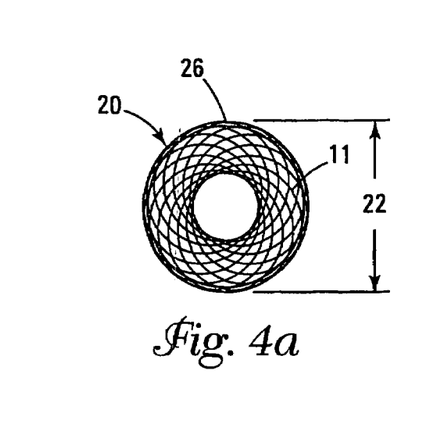
FIG. 4a shows an end view of the coated braid assembly shown in FIG. 4.

FIGS. 3, 3a, 4, 4a and 5 show a coated braid assembly 20 which defines a diameter 22 and a longitudinal dimension 24. The coated braid assembly 20 comprises a plurality of individual strands 11 that are crossed over each other to substantially form a cylinder as shown in FIG. 3 when in an unstressed or relaxed state. In a preferred embodiment, the coated braid assembly 20 is made of individual strands 11 of nitinol which is processed to display superelasticity at some point below normal human body temperature of 37 degrees C. Additional materials such as carbon fibers, stainless steel and composite materials would also work and are therefore within the scope of the invention. The coated braid assembly 20 is coated with an elastomeric coating 26 which serves to form a sealed tube capable of containing and conveying fluids. The diameter 22 and longitudinal dimension 24 of the coated braid assembly 20 are inversely proportional to each other, wherein as shown in FIG. 4 the coated braid assembly 20 upon being increased in its longitudinal dimension 24 decreases in at least some portion of its diameter 22.

Inversely, as shown in FIG. 3, when the coated braid assembly 20 is decreased in longitudinal dimension 24 the diameter 22 of the previously narrowed portion (unnumbered) increases. The braiding pattern as shown in FIGS. 3, 3a, 4 and 4a shows bilateral symmetry wherein a center portion (unnumbered) of the coated braid assembly 20 decreases in diameter with an increased longitudinal dimension 24. It should be noted that other braiding techniques and materials exist which would cause a different portion (not shown) of the coated braid assembly 20 to decrease in diameter 22 with an increased longitudinal dimension 24, resulting in a different symmetry.

Figure 5:
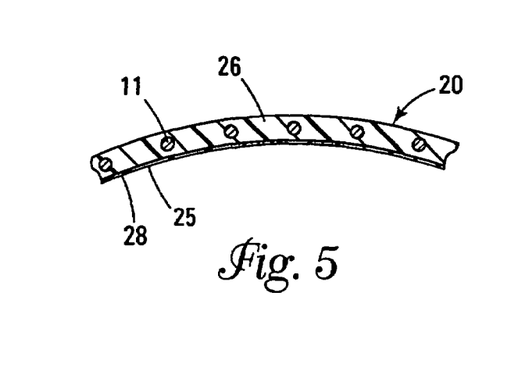

FIG. 5 shows a cross section of the coated braid assembly 20. The individual strands 11 of the coated braid assembly 20 are embedded in the elastomeric coating 26 which serves to bind the individual strands 11 together as well as sealing the cylinder formed by the strands 11 to form a sealed tube (unnumbered) capable of containing and conveying fluids. The interior surface 25 of the coated braid assembly 20 is further coated with an anti-thrombogenic coating 28 or a pro-endothelialization coating (not shown) which mimics the endothelialization which is part of the blood vessel's initmal lining and prevents or reduces blood clotting. Various substances can be used as anti-thrombogenic coating 28 in the present invention, including but not limited to heparin complex solutions, benzalkonium heparinate, tridodeclymethy-lammonium heparinate, chlorhexidine-silver sulfadiazine, mycocycline and rifampin. The elastomeric coating 26 can comprise many materials, such as a urethane, ePTFE or silicone material, which provide great strength and flexibility while remaining thin. The elastomeric coating 26 is applied to the uncoated braid 10 by any of several coating methods well known to those having ordinary skill in the art, including but not limited to, dipping, spraying, injection molding and coating over a mandrel to produce a smooth inner surface 25 of the coated braid assembly 20 prior to applying the anti-thrombogenic coating 28. Similarly, the anti-thrombogenic coating 28 can be applied by coating, spraying, dipping or vapor deposition processes.

Figure 6:
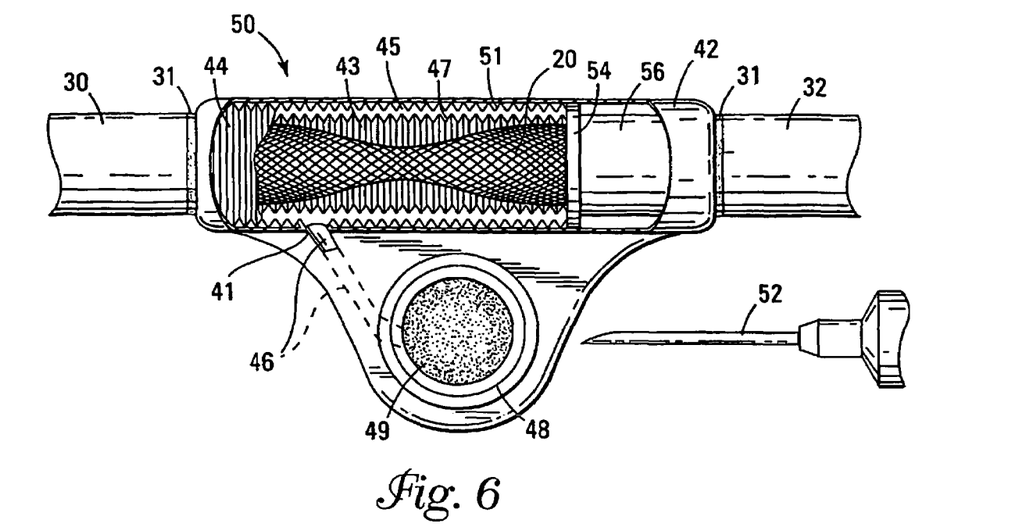
FIG. 6 shows a cut away plan view of the dialysis valve actuated by an elongatable/compressible bellows in the elongated, closed position.
Figure 6A:
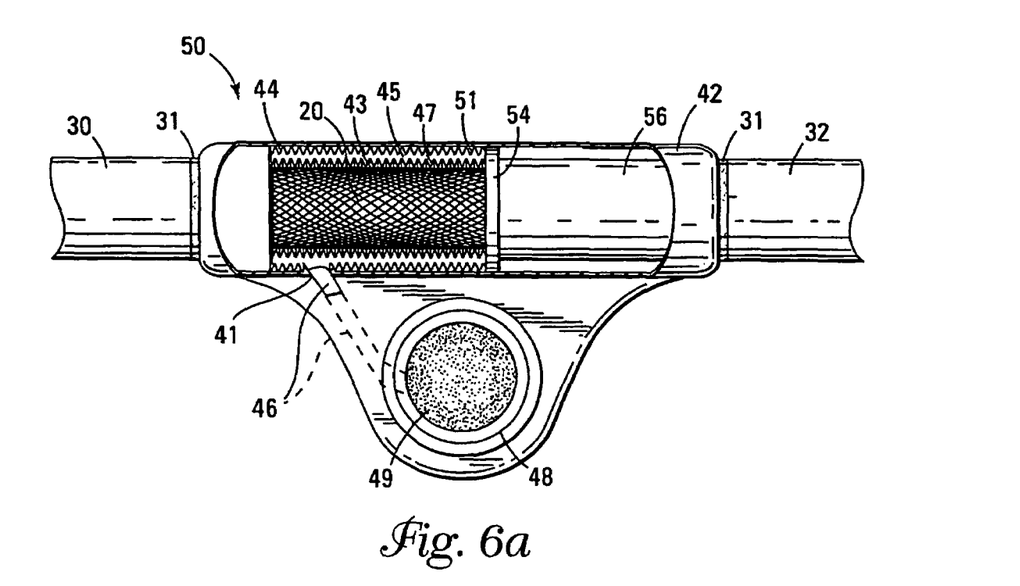
FIG. 6a shows a cut away plan view of the dialysis valve shown in FIG. 6 in the shortened, open position.

FIG. 6 shows a cut away plan view of an embodiment of the dialysis valve 50 actuated by a hydraulically actuated double walled metal bellows 44. The bellows 44 can be made of such materials as platinum, gold or stainless steel and can be made by vapor deposition over a wax mandrel. Two separate sized mandrels are used to produce a (smaller diameter) inner wall 47 and a (slightly larger diameter) outer wall 51. Silicone or urethane glue (not shown) is applied to a nipple 53 at a bonding area 31 extending from a floating connector 54 and/or fixed connector 55. The coated braid assembly 20 is then attached to the floating connector 54 and/or fixed connector 55 by inserting the coated braid assembly 20 over the nipple 53 extending from the floating connector 54 and/or fixed connector 55. The surface (unnumbered) of the nipple 53 may be knurled or have concentric grooves to facilitate attachment and sealing. An "O" ring 83 may be placed over the end (unnumbered) of the coated braid assembly 20 contacting the nipple 53 to further facilitate attachment and sealing. The coated braid assembly 20 with attached floating connector 54 and/or fixed connector 55 is then mounted inside a chamber 43 formed by the inner wall 47 of the bellows 44. At least one end (unnumbered) of the coated braid assembly 20 is attached to a floating connector 54. The floating connector 54 and/or fixed connector 55 provide that the ends (unnumbered) of the coated braid assembly 20 are maintained in an open configuration irrespective of the diameter of other portions of the coated braid assembly 20. It is contemplated to have both ends (unnumbered) of the coated braid assembly 20 attached to a floating connector 54. Alternatively, one end (unnumbered) of the coated braid assembly 20 can be attached to a floating connector 54 while the other end (unnumbered) is attached to a fixed connector 55. The inner wall 47 is inserted into the outer wall 51 and then laser-welded at the end (unnumbered) to a floating connector 54 at each end or a floating connector 54 at one end and a fixed connector 55 at the other end to seal the bellows 44. The floating connector 54 and fixed connector 55 are made of the same material as the inner wall 47 and outer wall 51 of the bellows 44. A hydraulic line 46 is attached to an aperture 41 extending through the outer wall 51 only. An inter-wall space 45 exists between the inner wall 47 and outer wall 51 of the bellows 44. In the view shown in FIG. 6 the coated braid assembly 20 and floating connectors 54 are disposed inside the chamber 43. In FIG. 6 the bellows 44 is longitudinally extended, which correspondingly increases the longitudinal dimension of the internally attached coated braid assembly 20. As shown in FIG. 4 when the coated braid assembly 20 is longitudinally extended at least a portion of it will assume a lesser diameter 22. It should be mentioned that the diameter 22 of the coated braid assembly 20 is dependent on its degree of longitudinal extension. The double walled bellows 44 is mounted in an outer housing 42 which is configured to provide space for the coated braid assembly 20 to elongate or shorten during actuation of the valve 50. Due to the varying longitudinal dimensions 24 the coated braid assembly 20 can assume, a compressible section 56 made of ePTFE is attached to the at least one floating connector 54. Alternately, if two floating connectors 54 are used, a second compressible section 56 will be used. One end (unnumbered) of the coated braid assembly 20 and attached floating connector 54 or fixed connector 55 is attached to compressible section 56 which is attached to the fistula graft (arterial) 30 while the other end (unnumbered) is attached to the fistula graft (venous) 32 or to a second compressible section 56. A bonding area 31 exists where an adhesive is alternatively used to further facilitate the attachment. The fistula grafts 30, 32 are made of ePTFE. A hydraulic line 46 is in fluid communication with the inner wall space 45 of the bellows 44 via the aperture 41 and extends to a port 48 which is covered by a membrane 49 which is made of a self-sealing material such as an implantable latex, urethane or silicone. The outer housing 42 is preferably injection molded implantable high durometer urethane plastic (Carbothane®) or machined stainless steel or other biocompatible plastic and metal materials could also be used. During actuation of the dialysis valve 50 a saline solution (not shown) is injected into the bellows 44 by means of a pressurizing infusion needle 52 which is inserted by a physician through the membrane 49 covering the port 48 via the hydraulic line 46. The bellows 44 is adjustable corresponding to the amount of saline injected and can thus be fully extended or assume any intermediate position. This causes the bellows 44 to extend longitudinally, thus simultaneously causing the coated braid assembly 20 to increase in longitudinal dimension 24 and at least a portion to decrease in its diameter 22, resulting in a controlled, reduced blood volume through the valve 50. The normal, default condition of the bellows 44 is in the foreshortened or open configuration as shown in FIG. 6a. Thus, should control of blood flow through the dialysis valve 50 fail for any reason, normal blood flow would resume.

FIG. 6a shows a cut away plan view of the dialysis valve 50 shown in FIG. 6 but with the coated braid assembly 20 in the shortened, open configuration.

Figure 6B:
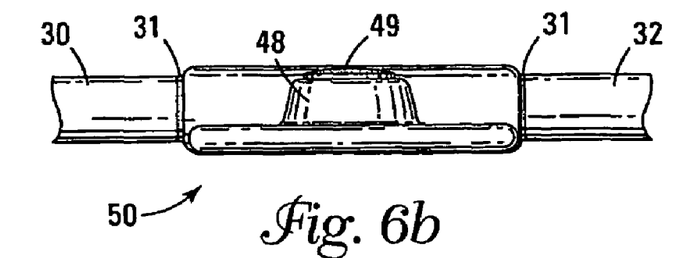
FIG. 6b shows a side view of the valve shown in FIG. 6.
Figure 6C:
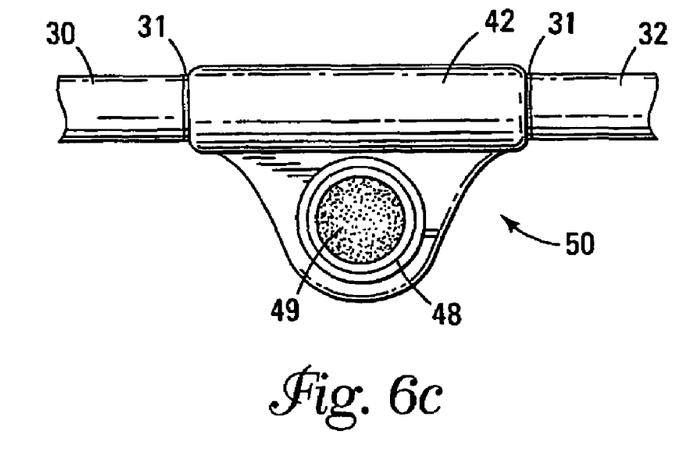
FIG. 6c shows a plan view of the valve shown in FIG. 6.
Figure 6D:
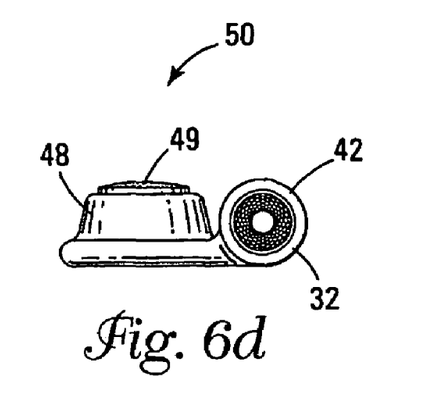
FIG. 6d shows an end view of the valve shown in FIG. 6.

FIG. 6b shows a side view of the dialysis valve 50. FIG. 6c shows a top view of the dialysis valve 50. FIG. 6d shows an end view of the dialysis valve 50.

Figures 7, 7A:
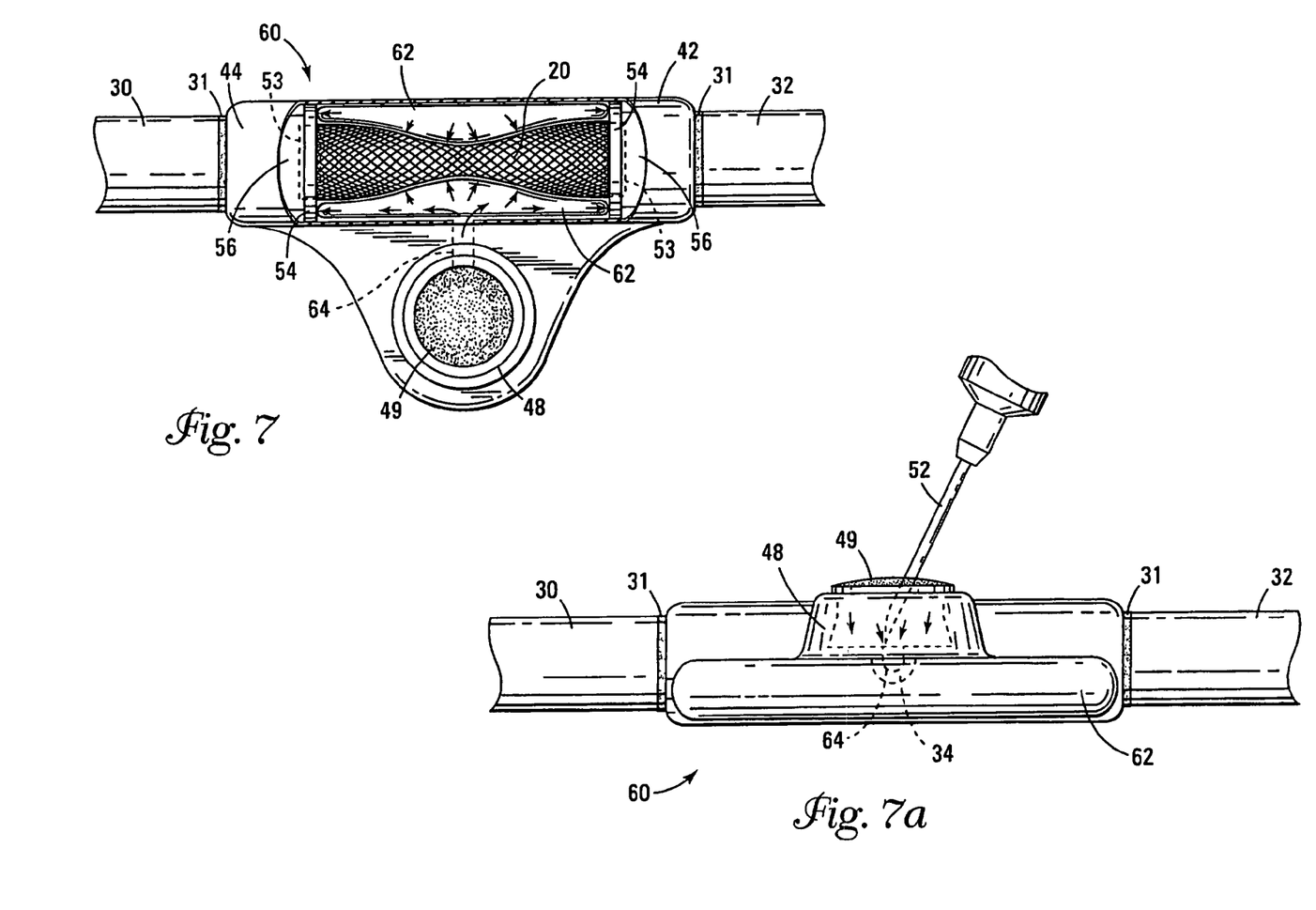
FIG. 7 shows a cut away plan view of the valve activated by an inflatable balloon.
FIG. 7a shows a side view of the dialysis valve shown in FIG. 7, with the infusion needle penetrating the membrane.

FIG. 7 shows a cut away plan view of an embodiment of the dialysis valve 60 which is actuated by means of a hydraulic balloon 62 which extends around the coated braid assembly 20 in a cuff-like manner. The balloon 62 can be made from elastomeric latex, silicone or urethane. In this embodiment of the dialysis valve 60 the coated braid assembly 20 is attached at each end to a floating connector 54. The floating connector 54 provides that the ends (unnumbered) of the coated braid assembly 20 are maintained in an open configuration regardless of the diameter of other portions of the coated braid assembly 20. The floating connector 54 is attached at at least one end to a compressible section 56 made of ePTFE within the outer housing 42. The compressible section 56 is attached to the floating connector 54 and provides for the increase or decrease of the longitudinal dimension 24 of the coated braid assembly 20 within the outer housing 42 during actuation of the valve 60. It should be mentioned that both ends of the coated braid assembly 20 may be provided with floating compressible sections 56. A port 48 is attached to the outer housing 42 and is covered by a membrane 49 which is made of a self-sealing material such as silicone or urethane. The outer housing 42 is preferably injection molded implantable high durometer urethane plastic or machined stainless steel, however, other biocompatible plastic and metal materials could also be used. A hydraulic line 64 connects balloon 62 to the port 48 which is covered by membrane 49. Actuation of the dialysis valve 60 is accomplished as shown in FIG. 7a by inserting an infusion needle 52 through the membrane 49 and injecting a pressurized saline solution (not shown) through the port 48 via the hydraulic line 64. The balloon 62 is adjustable corresponding to the amount of saline injected and can thus be fully inflated or assume any intermediate position. When the balloon 62 is mounted within the outer housing 42 this results in the balloon 62 radially expanding as well as elongating, which causes at least a portion of the coated braid assembly 20 to assume a decreased diameter 22, thus controlling the flow of blood through the dialysis valve 60. Radial compression is thus increased, precisely controlling the inward force of the inflated balloon 62 against the hemodynamic forces exerted against the inner surface 25 of the coated braid assembly 20. It should also be mentioned that in another embodiment, the balloon 62 and coated braid assembly 20 could be integrally attached at one or a plurality of locations (not shown).

FIG. 7a shows a side view of the dialysis valve 60 with the infusion needle 52 penetrating the memorane 49. Also shown in FIG. 7a is the connection of the hydraulic line 64 to the balloon 62.

Figure 8A:
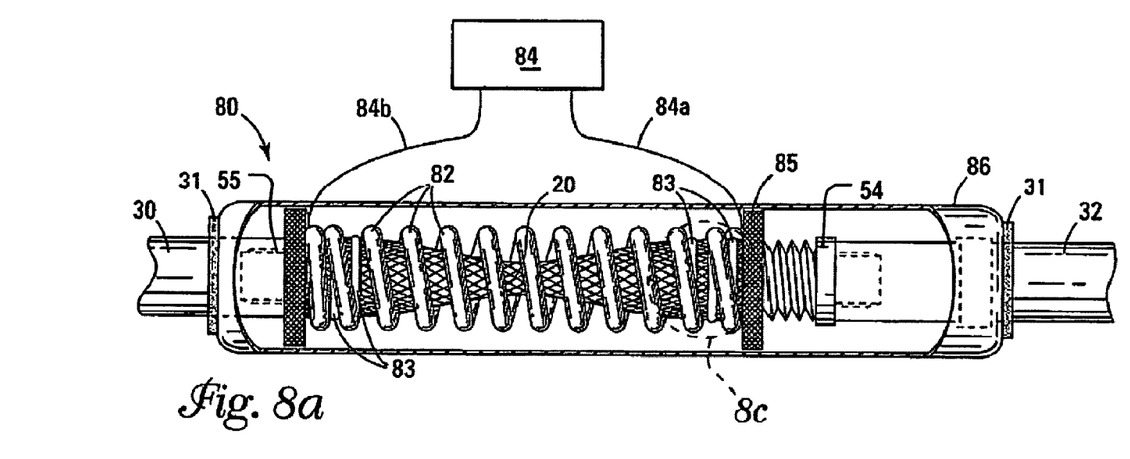
FIG. 8a shows a cut away side view of the valve with a nitinol coil spring in the elongated, narrowed configuration.
Figure 8B:
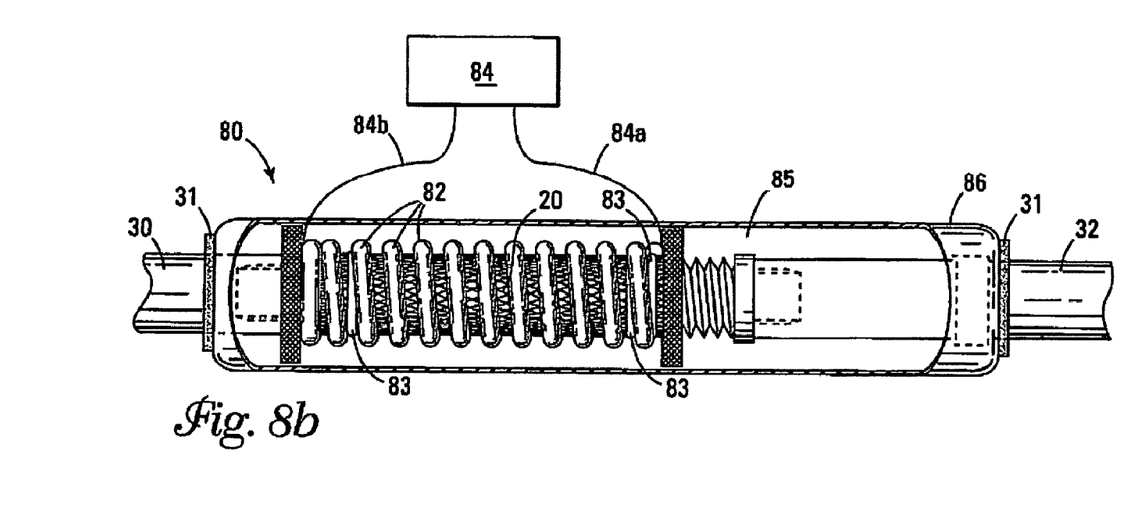
FIG. 8b shows a cut away side view of the valve with a nitinol coil spring in the shortened, open configuration.
Figure 8C:
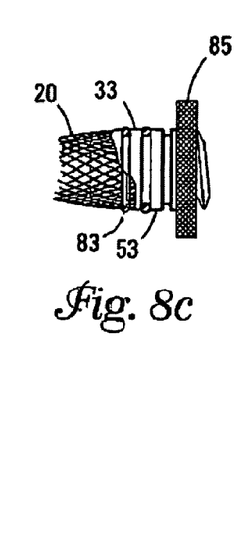
FIG. 8c is a partial breakaway side view of the nipple and threaded member attached to the coated braid assembly.

FIG. 8a shows a cut away side view of an embodiment of the valve 80 that is actuated by a nitinol spring 82 attached to at least one floating connector 54. The floating connector(s) 54 and/or fixed connector 55 is/are attached to each end (unnumbered) of the coated braid assembly 20 and serve as attachment points for the nitinol spring 82 as well as keeping the ends (unnumbered) of the coated braid assembly 20 in an open configuration at all times. Silicone or urethane glue (not shown) is applied at a bonding area 33 to a nipple 53 extending from the floating connector 54 and/or fixed connector 55. The coated braid assembly 20 is then attached to the floating connectors 54 by inserting the coated braid assembly 20 over the nipple 53 extending from the floating connector 54 and/or fixed connector 55. The surface (unnumbered) of the nipple 53 may be knurled or have grooves to facilitate attachment and sealing. A slip ring or "O" ring 83 may further be placed over the end (unnumbered) of the coated braid assembly 20 contacting the nipple 53 to further facilitate attachment and sealing. At least one end of the nitinol spring 82 and attached floating connector 54 is attached to a compressible section 56 of ePTFE to provide for longitudinal movement of the coated braid assembly 20 during actuation within the outer housing 86. At least one floating connector 54 is threadably engaged with a threaded connector 85 which serves to provide a means of adjustment for the amount of closure of the valve 80. A controller 84 which comprises an electrical power supply (not shown), regulator (not shown) and timer (not shown) is in electrical connection by means of signal wire 84a and ground wire 84b to respective ends of the nitinol spring 82. In a preferred embodiment, the electrical energy needed for actuating the nitinol spring 82 is supplied by a battery (not shown). Battery power is preferred because of portability, safety and low cost. When an appropriate amount of electrical energy is sent from the controller 84 to the nitinol spring 82 it will shorten from its default elongated (closed) configuration as shown in FIG. 8a, to its shortened (open) configuration as shown in FIG. 8b, thus causing a increased diameter 22 of the coated braid assembly 20 and an open flow through the valve 80.

Figure 9:
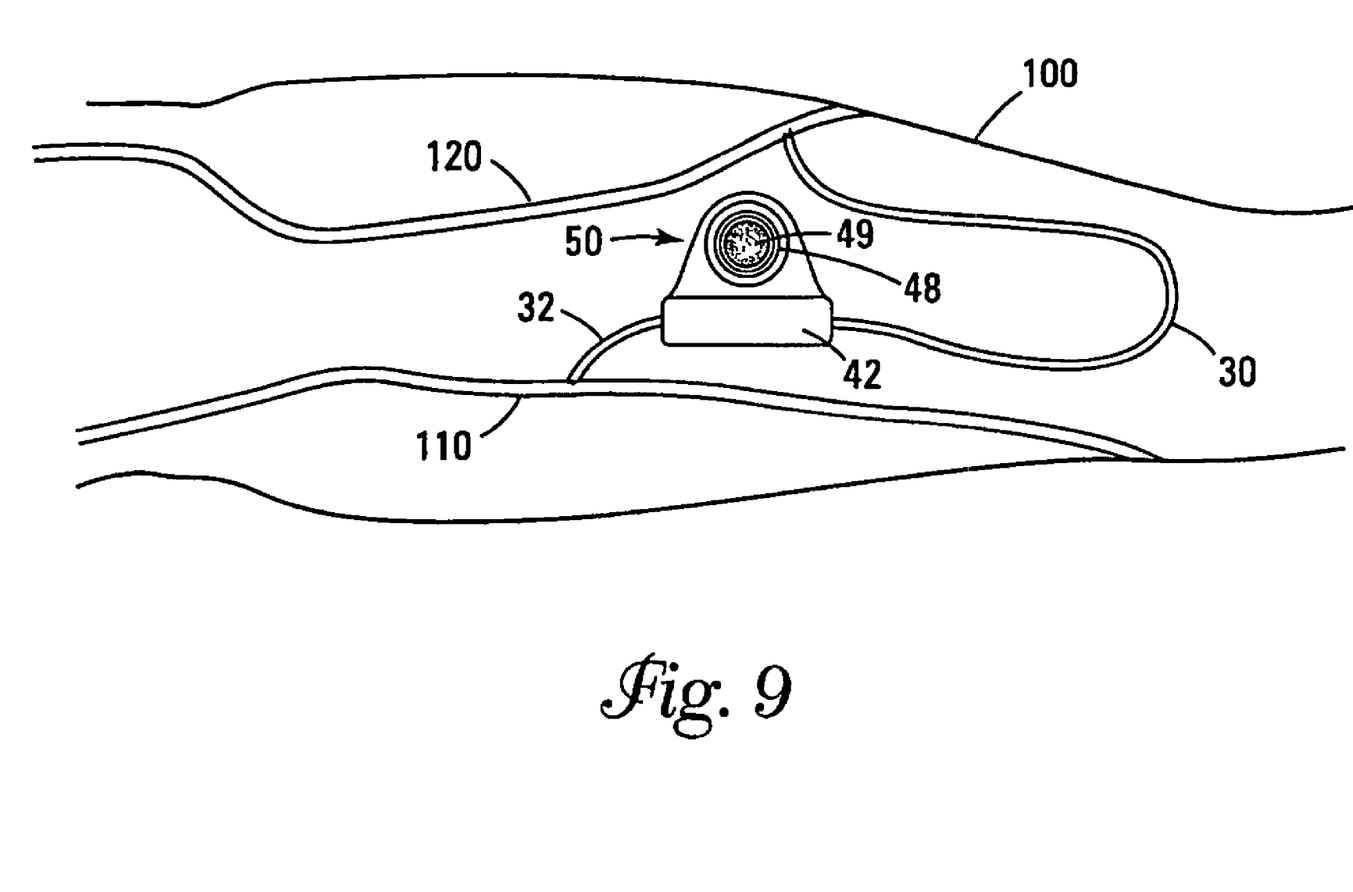
FIG. 9 shows a plan view of an embodiment of the valve sutured between a vein and an artery.

FIG. 9 shows a plan view of the dialysis valve 50 implanted into the arm 100 of a patient between an artery 110 and vein 120 to perform dialysis. While the dialysis valve 50 is shown in FIG. 9, the other embodiments are disclosed in the specification and, would be implanted in the patient in an identical manner.

Nitinol is an approximate stoichiometric alloy of nickel and titanium and is used in the invention for two different purposes, as discussed above. Other elements, however, such as vanadium are sometimes added in small amounts to alter the mechanical characteristics of the alloy. Chemical composition and processing history primarily determine the particular mechanical properties of a shape memory/superelastic metallic alloy. In general, such an alloy will exist in either one or the other, or combinations of two crystallographic phases. Austenite is the parent crystallographic phase and exists at higher temperatures. Martensite is the other phase and is formed by either subjecting the alloy to lower temperatures, electrical stress or by placing mechanical or physical stress on the alloy while it is in the austenitic phase. Transition temperatures between these two phases can be experimentally determined for a particular alloy. Processing history includes high temperature annealing as well as low temperature forming and deformation. Following standard material and processing specifications, the transitional temperatures that define the alloy's mechanical characteristics are predictable and controllable. Standard transitional temperature designations are given as: $M_s$ for the start of the transition to the martensitic phase, $M_f$ for completion of the transition to martensite, $A_s$ for the start of the transition to the austenitic phase, and $A_f$ for the completed transition to austenite.

Nitinol is trained into a desired shape by restraining the alloy into the desired shape, then baking the restrained alloy at relatively high temperatures for a specified period of time. Due to the variability in composition, desired mechanical characteristics and size of alloy used, temperatures and times will vary and overlap.

Superelasticity is based on the stress-induced phase transition from austenite to martensite. Stress-induced induced phase transition from austenite to martensite occurs when the alloy temperature is above $A_f$ and a physical restraint is applied to the alloy. As long as the restraint is in place, the portion of the alloy receiving the stress reverts to the martensitic phase, which remains as long as the stress is maintained. Unless the shape recovery limits are exceeded, when the restraint is removed and the stress is released the alloy returns to its original austenitic phase and trained shape as long as the temperature is maintained above $A_f$. Thus, when the austenitic, trained shape of the alloy is deformed and held by stress in a new shape, a certain amount of force is exerted by the alloy against the restraint as it resists the new, untrained shape.

The thermal shape memory effect of these alloys has been known much longer than superelasticity. Thermal shape memory occurs as the result of a piece of shape memory alloy metal being deformed while in the lower temperature martensitic phase and then being reheated to a temperature somewhere above $A_s$ which causes the alloy to reform in the austenitic phase. When the crystallographic nature of the alloy is completely austenitic, the alloy's shape returns to the previously trained shape. Shape memory training occurs when a thermal shape memory/superelastic metallic alloy is annealed (heat treated) while restrained in a certain shape. The trained shape will then be maintained unless it is deformed while in the low temperature martensitic phase. Upon reheating the alloy to the austenitic phase, the original shape, which was "learned" in the annealing process, will be "remembered" and returned to. Thus, temperature change is one way of controlling the crystallographic phase of a shape memory/superelastic metallic alloy. The nitinol spring 82 is actuated by electrical energy heating the alloy to resume the austenitic phase and thus its originally trained shape.

One practical advantage of a shape memory/superelastic alloy over non-superelastic materials is that it can be deformed to a far greater degree without taking a permanent set or kink. In the case of superelastic alloys (i.e., alloys processed to exhibit superelasticity at body temperature), assuming the alloy is above the $A_f$ temperature, removal of the restraint alone is sufficient to resume the original, trained shape. When the alloy is processed to have shape memory characteristics, the martensitic phase alloy need only be subjected to temperatures somewhere above $A_f$ and the alloy will eventually return to its original, trained shape. It is also possible to use a restraint in conjunction with alloys trained to exhibit thermal shape memory characteristics.

Thus, the-uncoated braid 10 that forms the reinforcement of the coated braid assembly 20 made of nitinol is processed to exhibit superelastic characteristics at human body temperature. More specifically, superelasticity (stress-induced martensite) allows the coated braid structure 20 to repeatedly increase and decrease its longitudinal dimension 24 while simultaneously decreasing and increasing its 20 diameter 22 without taking a permanent set or kink. Finally, breaking as a result of metal fatigue is virtually unknown with superelastic nitinol.

Use

The dialysis valve 50, 60 is incorporated into a dialysis fistula system to close or limit the flow of blood during periods when dialysis is not taking place. Using techniques which are well known, the fistula is inserted between a vein 120 and an artery 110. The dialysis valve 50, 60 is only open when dialysis is occurring. As explained above, between dialysis treatments the dialysis valve 50, 60 may be constricted allowing a limited, increased velocity blood flow thereby preventing the formation of thrombus or clotting in the fistula. In other instances, the valve 50, 60 may be completely closed, preventing any blood flow between dialysis treatments.

Using the dialysis valve 50, 60 following successful surgical implantation first requires the physician locating the port 48 and membrane 49 which are located beneath the patient's skin. Between dialysis treatments an infusion needle 52 loaded with a saline solution first punctures the patient's skin followed by puncturing the membrane 49. The saline solution (not shown) is then injected under pressure through the port 48, hydraulic line 46, 64 and finally into the bellows 44 or balloon 62. Saline is continued to be injected until the desired degree of closure of the coated braid assembly 20 is achieved. When the next dialysis treatment is to occur, the physician locates the port 48 and membrane 49, inserts an infusion needle 52 and withdraws the saline solution, resulting in the coated braid assembly 20 decreasing in its longitudinal dimension 24 and increasing in diameter, thus resuming its open, default configuration.

Although the present invention has been described in considerable detail with reference to certain preferred versions thereof, other versions are also possible. Therefore, the spirit and scope of the appended claims should not be limited to the description of the preferred versions contained herein.

What is claimed is:

1. An implantable dialysis valve for fluid connection between an artery and a vein, comprising:
    an implantable tube to convey blood from an arterial connection end to a venous connection end, the tube extending for a longitudinal length;
    an actuation port to receive a fluid through a self-sealing membrane for adjustment of the longitudinal length of the tube; and
    a hydraulically actuated bellows in fluid communication with the actuation port so as to adjust from a first length to a second length when the fluid is received through the membrane in the actuation port, the bellows being coupled with the tube so that when the bellows adjusts from the first length to the second length, the tube contemporaneously increases in longitudinal length and decreases in diameter at a narrowed portion, wherein the narrowest portion of the tube decreases in diameter while not fully closing.

2. The dialysis valve of claim 1 wherein the tube comprises a braided nitinol structure processed to exhibit superelasticity below normal human body temperature, the braided nitinol structure having an elastomeric coating, wherein the tube is repeatedly adjustable in longitudinal length and diameter.

3. The dialysis valve of claim 2 wherein the tube defines an inner surface that is substantially smooth and is coated with an anti-thrombogenic coating.

4. The dialysis valve of claim 3 wherein the bellows is double walled so as to define an inner wall space in fluid communication with the actuation port so that when fluid is urged into the inner wall space, the bellows increases in length and thereby actuates the tube to contemporaneously increase in longitudinal dimension and decreases in diameter at the narrowed portion.

5. The dialysis valve of claim 4 further comprising an implantable housing sized to fit between an artery and a vein when implanted, the housing containing the tube and the bellows, wherein the actuation port is attached to the housing such that the membrane is adjacent to skin when the housing is implanted.

6. The dialysis valve of claim 3, wherein the tube decreases in diameter at a narrowest portion while not fully closing to provide a blood flow rate through the tube of less than about 300 cc per minute when the tube is connected between an artery and a vein.

7. The dialysis valve of claim 1 wherein the tube is mounted to the bellows so that when the bellows is actuated to increase in length, the tube contemporaneously increases in longitudinal dimension and decreases in diameter at the narrowed portion.

8. An implantable dialysis valve for fluid connection between an artery and a vein, comprising:
    an implantable housing sized to fit between an artery and a vein;

an arterial fistula graft connected with the housing to attach with the artery when the housing is implanted;

a venous fistula graft connected with the housing to attach with the vein when the housing is implanted;

an adjustable tube arranged in the implantable housing to convey blood from the arterial fistula graft to the venous fistula graft, the tube extending for a longitudinal length and defining an inner surface that is substantially smooth and is coated with an anti-thrombogenic coating, wherein the tube comprises a braided nitinol structure having an elastomeric coating;

an actuator to selectively adjust from a first length to a second length in response to fluid or electric control, the actuator being coupled with the tube so that when the actuator adjusts from the first length to the second length, the tube contemporaneously increases in longitudinal length and decreases in diameter at a narrowed portion.

9. The dialysis valve of claim 8 wherein the tube decreases in diameter at the narrowed portion while not fully closing the tube.

10. The dialysis valve of claim 9 wherein the tube decreases in diameter at the narrowed portion while not fully closing the tube to blood flow so that the tube operable to constrict and provide blood flow therethrough at an increased velocity to hinder the formation of thrombus or clotting.

11. The dialysis valve of claim 10 wherein the tube decreases in diameter at a narrowest portion while not fully closing to provide a blood flow rate through the tube of less than about 300 cc per minute when the tube is implanted between an artery and a vein.

12. The dialysis valve of claim 8 wherein the actuator comprises a fluid controlled bellows that adjusts from the first length to the second length, the bellows being in fluid communication with an actuation port that receives fluid through a self-sealing membrane for adjustment of the longitudinal length of the tube.

13. The dialysis valve of claim 12 wherein bellows is double walled so as to define an inner wall space in fluid communication with the actuation port so that when fluid is urged into the inner wall space, the bellows increases in length and thereby actuates the tube to contemporaneously increase in longitudinal length and decrease in diameter at the narrowed portion.

14. The dialysis valve of claim 12 wherein the actuation port is attached to the housing such that the membrane is adjacent to skin when the housing is implanted.

15. The dialysis valve of claim 8 wherein the actuator comprises an inflatable balloon adjustable to various degrees of inflation, the balloon acting upon the tube so that, when the balloon is inflated, the tube contemporaneously increases in longitudinal length and decreases in diameter at the narrowed portion.

16. The dialysis valve of claim 8 wherein the actuator comprises an adjustable nitinol spring attached to the tube such that, when the spring is controlled to shift from the first length to the second length, the tube contemporaneously increases in longitudinal length and decreases in diameter at the narrowed portion.

17. A method of controlling blood flow between and during dialysis treatments, comprising:

a. implanting a dialysis valve comprising a tube between a patient's vein and an artery, the tube operable to convey fluids and defining a longitudinal dimension, a diameter and an inner surface, wherein the dialysis valve further comprises a bellows capable of being held at varying lengths, the bellows defining an interior chamber wherein the tube is mounted in the chamber so that when the bellows adjustably increases in length, the tube simultaneously increases in longitudinal dimension and at least a portion of the tube decreases in diameter;

b. narrowing the diameter of the tube in an adjustable manner between dialysis treatments at at least one location along the longitudinal dimension, wherein the diameter of the tube is narrowed while not fully closing the diameter to thereby provide blood flow through the tube between dialysis treatments; and c. opening the diameter of the tube at the narrowed location by adjustably changing the longitudinal dimension of the tube to conduct a dialysis treatment, wherein the diameter of the tube is opened to thereby provide increased blood flow through the tube during the dialysis treatment.

18. The method of claim 17 wherein the tube comprises a braided nitinol structure processed to exhibit superelasticity below normal human body temperature coated with an elastomer allowing the tube to be repeatedly altered in longitudinal dimension and in diameter and still maintain fluid containing capability.

19. The method of claim 18 wherein the inner surface of the tube at the narrowed location is in a substantially circular configuration.

20. The method of claim 17 wherein the inner surface of the tube is substantially smooth and comprises an anti-thrombogenic coating.

21. The method of claim 17 wherein the bellows is double walled so as to define an inner wall space; a hydraulic line is in fluid connection with the inner wall space so when a pressurized fluid is pumped into the inner wall space, the bellows increases in length, simultaneously increasing the longitudinal dimension of the tube.

22. The method of claim 17 wherein the diameter of the tube is narrowed to provide blood flow through the tube between dialysis treatments at a blood flow rate of less than about 300 cc per minute.

* * * * *